United States Patent [19]

Baines et al.

[11] 4,279,889

[45] Jul. 21, 1981

[54] PERIODONTAL DENTAL COMPOSITION

[75] Inventors: Eric Baines, Flixton; Kenneth Harvey, Wilmslow, both of England

[73] Assignee: Colgate-Palmolive Company, New York, N.Y.

[21] Appl. No.: 143,066

[22] Filed: Apr. 24, 1980

[30] Foreign Application Priority Data

May 15, 1979 [GB] United Kingdom ............... 16873/79

[51] Int. Cl.$^3$ .......................... A61K 7/16; A61K 7/18
[52] U.S. Cl. ....................................... 424/57; 424/49; 424/52
[58] Field of Search ..................................... 424/48–58

[56] References Cited

FOREIGN PATENT DOCUMENTS 2242553  3/1974  Fed. Rep. of Germany .

OTHER PUBLICATIONS

Slovokhotnova Chem. Abstr. 71, #10826(d), (1969), Role of B-Vitamins in Preventing Dental Caries.
Vogel et al., Chem. Abstr. 86, #657455, (1977), The Effect of Folic Acid on Gingival Health.
Dreizon et al., J. Dent. Res. 44(3): 616–620, May, Jun. 1970, The Effect of Folic Acid Deficiency on Marmoset Oral Mucosa.
Abstr. in Chem. Abstr. 73, #106848e, (1970).
Koehlor Chem. Abstr. 80, #149035z, (1974) of Ger. Off. 2,342,533, Mar. 7, 1974.

*Primary Examiner*—Shep K. Rose
*Attorney, Agent, or Firm*—Robert L. Stone; Murray M. Grill; Herbert S. Sylvester

[57] ABSTRACT

A periodontal dental composition is disclosed comprising folic acid and a polishing agent which is principally dicalcium phosphate.

6 Claims, No Drawings

PERIODONTAL DENTAL COMPOSITION

Folic acid is a well known anti-irritant and anti-inflammatory material. A normal adult requires at least about 0.3 mg of this material in order to maintain oral health. Folic acid is a conjugate bound to up to seven molecules of glutamic acid. It has the structural formula:

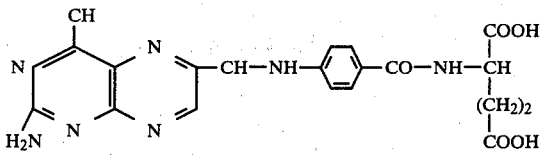

It was reported by R. Vogel et al of New Jersey Dental School, Newark, N.J., in AADR Abstracts 1977, 34 "Effect of Folic Acid Rinse On Gingival Health" and IADR Abstracts 1977, 565 "Folic Acid and Experimental Produced Gingivitis", that folic acid can be directly absorbed by the gingiva from a rinse solution resulting in a significant reduction in gingival inflammation.

Unfortunately, when a dental preparation is formulated including a dentally acceptable water-insoluble polishing agent the retention of soluble folic acid available to be absorbed in the gingiva can be substantially reduced.

According to the present invention a periodontal dental composition comprises folic acid and a polishing agent which is principally dicalcium phosphate.

The periodontal dental composition comprising folic acid and polishing agent is typically a dental cream. The initial pH of the preparation may be about 4–10, preferably about 6–9 (on a 20% slurry). Below a pH of about 4, large amounts of folic acid would be removed.

Folic acid is typically present in amount of about 0.01–5% by weight, preferably about 0.05–0.5%.

Various water-insoluble polishing agents which are normally dentally acceptable cause removal of at least a portion of the folic acid from solution in the composition. For instance, sodium aluminosilicate (e.g. of low alumina content; essentially sodium silicate with a small amount of combined alumina) and insoluble sodium metaphosphate may cause insolubility or remove about 70% or more of the folic acid upon aging for 3 months at room temperature and at 43° C. Lesser, but still meaningful amounts of folic acid (e.g. about 15–25%) may be insolubilized or removed when the polishing material is hydrated alumina (e.g. alpha-alumina trihydrate) or calcium carbonate.

It has however been found that the polishing agent dicalcium phosphate permits high retention of soluble acid when it is the principal polishing agent. Indeed, when dicalcium phosphate, as the dihydrate or anhydrous salt, or as a mixture of both, is substantially the sole polishing agent compatibility with folic acid of up to 100% can be achieved upon aging for 3 months at room temperature, as well as often at 43° C.

The polishing agent typically comprises 20–75% by weight of the dental composition, preferably 20–55% by weight. Dicalcium phosphate is the principal component of the polishing agents; i.e., it comprises more than half to substantially all of the polishing agent.

The dental composition can be a cream or gel with liquids and solids proportioned to form a creamy or gel mass of desirable consistency. In general, liquids in the composition comprise chiefly water and humectants such as glycerine, sorbitol, propylene glycol, polyethylene glycol (e.g. molecular weight about 600) or the like, including suitable mixtures thereof. It is advantageous usually to use a mixture of both water and a binder or humectant such as glycerine and/or sorbitol. It is preferred to use at least about 30% liquid, preferably for a cream about 10–50% water, and about 20–80% humectant.

The solid portion of the vehicle is a gelling agent, such as the natural and synthetic gums and gumlike materials, such as Irish moss, gum tragacanth, alkali metal carboxymethyl cellulose and hydroxyethyl carboxymethyl cellulose, polyvinyl pyrrolidone, starch, xanthan, water-soluble hydrophilic colloidal carboxyvinyl polymers, such as those sold under the trademark Carbopol 934 and 940 and synthetic inorganic silicated clays such as those sold under the trademark Laponite CP and Laponite SP. These grades of Laponite have the formula

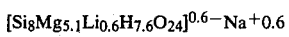

The solid portion of the vehicle is typically present in an amount up to about 10% by weight of the dentifrice and preferably about 0.5–5% by weight. When employed, grades of Laponite are preferably used in amounts of about 1–5% by weight.

Organic surface-active agents may be used in the composition of the present invention to achieve increased prophylactic action, assist in achieving through and complete dispersion of the instant compositions throughout the oral cavity, and render the instant compositions more cosmetically acceptable. The organic surface-active material may be anionic, nonionic, ampholytic or cationic in nature, and it is preferred to employ as the surface-active agent a detersive material which imparts to the composition detersive and foaming properties. Suitable types of such detergents are water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid ester of 1,2-dihydroxy propane, sulphonates, and the substantially saturated higher aliphatic acyl amides of lower aliphatic amino carboxylic acid compounds such as those having 12 to 16 carbon atoms in the fatty acid, alkyl or acyl radicals and the like. Examples of the last mentioned amides are N-lauroyl sarcosine, and the sodium, potassium, and ethanolamine salts of N-lauroyl, N-myristoyl or N-palmitol sarcosine, which should be substantially free from soap or similar higher fatty acid material which tends to substantially reduce the effect of these compounds in compositions of the present invention. The amides are particularly advantageous since they exhibit a prolonged and marked effect in the inhibition of acid formulation in the oral cavity due to carbohydrates breakdown in addition to exerting some reduction in the solubility of tooth enamel in acid solutions. Another desirable material is a long chain fatty acid sodium monoglyceride sulphonate used alone or in combination with sodium lauryl sulphate.

Other particularly suitable surface-active materials include nonionic agents such as condensates of sorbitan monostearate with approximately 60 moles of ethylene oxide, condensates of propylene glycol ("Pluronics") and amphoteric agents such as quaternized imidazole derivatives, which are available under the trademark "Miranol" such as Miranol C$_2$M. Cationic surface-active germicides and antibacterial compounds such as di-isobutyl phenoxy ethoxy ethyl dimethyl benzyl ammonium chloride, benzyl dimethyl stearyl ammonium chloride, benzyl dimethyl stearyl ammonium chloride, tertiary amines having one fatty alkyl group (of from 12-18 carbon atoms) and two (poly) oxyethylene groups attached to the nitrogen (typically containing a total of from about 2 to 50 ethanoxy groups per molecule) and salts thereof with acids, and compounds of the structure

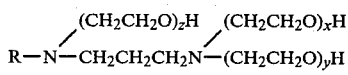

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the instant oral compositions.

Any suitable flavoring or sweetening materials may be employed in formulating a flavor for the composition of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsilicylate. Suitable sweetening agents include sucrose, lactose, maltose, sorbitol, sodium cyclamate, perillartine and saccharine. Suitably, flavor and sweetening agents may together comprise from about 0.01 to 5% or more of the compositions of the instant invention. Chloroform may be used too.

The composition of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride (SnF$_2$KF), sodium hexaflurorostannate, stannous chlorofluoride, sodium fluorozirconate, and sodium monofluorophosphate. These materials which disassociate or release fluorine-containing ions in water, suitably may be present in an effective but non-toxic amount, usually within the range of about 0.01 to 1% by weight of the water soluble fluorine content thereof.

The preferred fluorine-containing compounds are sodium fluoride, typically present in an amount of 0.02-2% by weight preferably about 0.24%, and sodium monofluorophosphate typically present in an amount of 0.076 to 7.6% by weight, preferably 0.8%.

Various other materials may be incorporated in the oral compositions of this invention. Examples thereof are coloring or whitening agents or dyestuffs, preservatives, anti-corrosive agents, silicones, chlorophylic compounds, ammoniated materials such as urea, diammonium phosphate and mixtures thereof and other constituents. Whitening agents, such as titanium dioxide, typically in amounts of about 0.5-2%, may be beneficial to the appearance of the dental composition, since upon aging, some discoloration may occur.

The adjuvants are incorporated in the instant compositions in amounts which do not substantially adversely affect the properties and characteristics desired and are selected and used in proper amounts depending upon the particular type of composition involved.

Antibacterial agents may also be employed in the oral compositions of the instant invention in an amount of about 0.01-5% by weight. Typical antibacterial agents include:

N$^1$-(4-chlorobenzyl)-N$^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-N$^5$-chlorobenzylbiguanide;
1,6-di-chlorophenylbiguanidohexane;
1,6-bis-(2-ethylhexylbiguanide) hexane;
1-(lauryldimethylammonium)-8-(p-chlorobenzyldimethylammonium) octane dichloride;
5,6-dichloro-2-guanidinobenzimidazole;
N$^1$-p-chlorophenyl-N$^5$-laurylbiguanide;
5-amino-1,3-bis(2-ethylhexyl)-5-methylhexahydropyrimidine and their non-toxic acid addition salts.

Synthetic finely divided silicas such as those sold under the trademarks Cab-O-Sil M-5, Syloid 244, Syloid 266 and Aerosil D200 and mixtures thereof may also be employed in amounts of about 0.5-20% by weight to promote thickening or gelling of the dentifrice.

The following specific Examples are illustrative of the present invention. All amounts are by weight unless otherwise indicated.

EXAMPLES 1-3

The following periodontal dental compositions were prepared and deaerated.

|  | 1 PARTS | 2 PARTS | 3 PARTS |
|---|---|---|---|
| Glycerine | 22.0 | 22.0 | 22.0 |
| Sodium carboxymethyl cellulose | 0.9 | 0.9 | 0.9 |
| Tetrasodium pyrophosphate | 0.5 | 0.5 | 0.5 |
| Sodium fluoride | — | 0.24 | — |
| Sodium monofluorophosphate | — | — | 0.82 |
| Sodium saccharine | 0.17 | 0.17 | 0.17 |
| Water | 20.67 | 20.43 | 19.85 |
| Dicalcium phosphate dihydrate | 48.76 | 48.76 | 48.76 |
| Flavor | 1.00 | 1.00 | 1.00 |
| Sodium lauryl sulphate (100%) | 1.50 | 1.50 | 1.50 |
| Folic acid | 0.50 | 0.50 | 0.50 |
| pH | 6.9 | 7.0 | 6.7 |

After aging for 3 months at room temperature and 43° C. the following retention levels of soluble folic acid are observed:

|  | % SOLUBLE FOLIC ACID RETENTION | |
|---|---|---|
| COMPOSITION | ROOM TEMPERATURE | 43° C. |
| 1 | 100.0 | 102.0 |
| 2 | 108.0 | 100.0 |
| 3 | 104.0 | 96.0 |

Complete retention of soluble folic acid upon aging at room temperature is also obtained when stannous fluoride (in amounts corresponding to 0.1% fluoride) replaces sodium fluoride in composition B. Color of compositions 1 to 3 can be improved by adding 1% titanium dioxide to each.

We claim:

1. A periodontal dental composition consisting essentially of about 0.01-5% by weight of folic acid and a polishing agent which is principally dicalcium phosphate.

2. The periodontal dental composition claimed in claim 1 which is a dental cream and has a pH in the range of 4-10.

3. A periodontal dental composition as claimed in claim 1 wherein 20-75% by weight of polishing agent is present.

4. A periodontal dental composition as claimed in claim 1 wherein the polishing agent is substantially solely dicalcium phosphate as the dihydrate or anhydrous salt, or as a mixture thereof.

5. A periodontal dental composition as claimed in claim 1 wherein the dicalcium phosphate is dicalcium phosphate dihydrate.

6. A periodontal dental composition as claimed in claim 1 wherein titanium dioxide is present.

* * * * *